United States Patent [19]

Smith

[11] 4,438,123
[45] Mar. 20, 1984

[54] OPHTHALMIC COMPOSITIONS OF CARBONIC ANHYDRASE INHIBITORS FOR TOPICAL APPLICATION IN THE TREATMENT OF ELEVATED INTRAOCULAR PRESSURE

[75] Inventor: Robert L. Smith, Lansdale, Pa.

[73] Assignee: Merck & Co., Inc., Rahway, N.J.

[21] Appl. No.: 333,273

[22] Filed: Dec. 22, 1981

Related U.S. Application Data

[63] Continuation of Ser. No. 128,439, Mar. 4, 1980, abandoned.

[51] Int. Cl.³ .............................................. A61K 31/425
[52] U.S. Cl. ..................................................... 424/270
[58] Field of Search ......................................... 424/270

[56] References Cited

U.S. PATENT DOCUMENTS

| | | | |
|---|---|---|---|
| 2,783,240 | 2/1957 | Vaughan et al. | 260/306.8 D |
| 2,835,702 | 5/1958 | Schultz | 260/556 |
| 3,949,082 | 4/1976 | Shen | 424/270 |

OTHER PUBLICATIONS

Amer. J. Ophthalmol., 39, 336–339, (1955), Foss.
Chem. Abst., 77, 105, 602(r), (1972), Roux.
Chem. Abst., 85, 56, 712(f), (1976), Maren.
Ocular Pharm.–Havener et al., pp. 395–419, (1966).
AMA–Achives of Ophth. 51, (6), 735–3739 (1954).
Amer. J. Ophthalmol. 47, 342–361, (1959), Beakes.
Brit. J. Ophthalmol. 39, 647–658, (1955), Gloster et al.
Amer. J. Ophthalmol. 44, (Part II), 388–402, (1957), Green et al.
Arzneim–Forsh, (Drug Res.), No. 5, 1975, "Effects of Topically Instilled Drugs on IOP in Rabbits" Silvestrini et al.

*Primary Examiner*—Douglas W. Robinson
*Attorney, Agent, or Firm*—Edmunde D. Riedl; William H. Nicholson; Mario A. Monaco

[57] ABSTRACT

Although dibasic carbonic anhydrase inhibitors (C.A.I.) can be administered systemically by oral or intravenous routes, attempts to administer them topically were inadvisable because of their elevated pH. The mono-alkali metal salts in the treatment of intraocular hypertension especially the sodium and potassium salts, of dibasic salt-forming C.A.I. are as effective in lowering intraocular pressure as dialkali metal salts of dibasic C.A.I. while having a pH more in harmony with ocular pH. They are found particularly useful when administered in conjunction with an ophthalmologically acceptable water-soluble polymer such as hydroxypropylcellulose in an aqueous carrier.

12 Claims, No Drawings

OPHTHALMIC COMPOSITIONS OF CARBONIC ANHYDRASE INHIBITORS FOR TOPICAL APPLICATION IN THE TREATMENT OF ELEVATED INTRAOCULAR PRESSURE

This is a continuation, of application Ser. No. 128,439 filed Mar. 4, 1980 now abandoned.

DISCLOSURE OF THE INVENTION

This invention relates to compositions of carbonic anhydrase inhibitors that are topically effective in the treatment of elevated intraocular pressure. More particularly, it relates to compositions comprising the monoalkali metal salts of dibasic salt-forming carbonic anhydrase inhibitors that, when applied topically to the eye, are transported to the ciliary process. In particular, this invention relates to compositions of the mono-sodium and mono-potassium salts of dibasic salt-forming carboxy anhydrase inhibitors and their use to lower intraocular pressure, especially in the treatment of ocular hypertension and glaucoma.

Glaucoma is a degenerative disease of the eye wherein the pressure within the eye (i.e., intraocular pressure) is too high for the normal function of the eye and, as a result, damage occurs to the optic nerve head resulting in irreversible loss of visual function. If untreated, glaucoma will eventually lead to blindness. Ocular hypertension, i.e., the condition of elevated intraocular pressure without optic nerve head damage of characteristic glaucomatous visual field loss, is now believed by the majority of ophthalmologists to merely represent the earliest phase in the onset of a glaucoma.

A number of the drugs presently employed to treat glaucoma are not entirely satisfactory, particularly in the earliest course of the disease when the side effects they produce are often worse than the symptoms of the disease.

Pilocarpine, a topical drug, although systemically harmless and quite effective, causes considerable local difficulties. The pupil constricts so that little light becomes available to the eye and the eye loses its ability to adapt from light to dark. Accommodation is stimulated so that the patient's refraction is sometimes incorrect and vision is blurred. The drug itself causes a local vasodilation and red eyes and irritation are common. In short, although valuable, it really is unsatisfactory as a first line drug.

When carbonic anhydrase inhibitors are used systemically they have a number of disadvantages. While extremely effective in lowering intraocular pressure, they often cause a numbness and tingling, gastrointestinal upsets and, frequently, depression, lethargy, and a loss of appetite, and general malaise. These, in addition to the occasional more severe systemic complications such as aplastic anemia, are so common that many physicians are reluctant to routinely prescribe carboxy anhydrase inhibitors. As a consequence, only highly motivated patients who understand the seriousness of their condition will faithfully continue medication.

While investigators have long realized the benefits that would accompany topical administration, the selection of the proper entity has long eluded them. Most reports in the literature indicate that carbonic anhydrase inhibitors are inactive topically. Even the extreme measure of direct injection into the anterior chamber is reported to have no pressure lowering effect.

Silvestrini, "Effects of Topically Instilled Drugs on Intraocular Pressure in Rabbits", Arzeim.-Forsch. (Drug Res.)25,Nr.5(1975), teaches that the disodium salts of acetazolamide can be used to lower the intraocular pressure of the normal rabbit eye. Silvestrini does, however, fail to confront the problem associated with the high pH of the disodium salt solutions and their high-likelihood of severe irritation and potential damage to the eye.

In the face of this collection of negative findings, it is now discovered that if monoalkali metal salt, most preferably the sodium or potassium salt, of a dibasic carbonic anhydrase inhibitor is employed as a topical agent, the pressure-lowering effects are substantially equivalent to systemic administration of the parent drug.

Because carbonic anhydrase inhibitors have a profound effect in altering basic metabolism, the avoidance of a systemic route serves to diminish, if not entirely eliminate, those side effects caused by metabolic acidosis such as vomiting, numbness, tingling, and general malaise and the like.

Furthermore, aqueous solutions of the dialkali metal salts are found to have a pH in excess of 10. Authors have asserted that if it is necessary to use a pH markedly at variance with the eye's normal pH of 7.4, medication is not well tolerated by the patient. Some consequences of applying medicaments with elevated pH's may be stinging, tissue irritation accompanied by loss of medication due to its being washed from the eye because of excessive tear production. While some alteration of the pH of a formulation of a dibasic salt of a carbonic anhydrase inhibitor can be achieved, it is recognized that this expedient has limits that effect the stability, solubility, and efficacy of the medicament.

In the practice of this invention, the alkali metal salts of carbonic anhydrase inhibitor are prepared from the known, salt-forming carbonic anhydrase inhibitors, the following of which are preferred: dichlorophenamide monosodium salt, dichlorphenamide monopotassium salt, acetozolamide monosodium salt and acetozolamide monopotassium salt. As used herein, the term "alkali metal" includes lithium, sodium, potassium, cesium and rubidium, particularly sodium and potassium.

These salts may be hygroscopic and, as a consequence, may occur as hydrated species. However, when used in aqueous isotonic ophthalmic formulations, hygroscopicity is obviously no longer a problem. When formulating into an insert, the material should be kept as dry as possible during manufacture and protected from excessive moisture during storage and before use. The preferred alkali metal salts include as cations, potassium, sodium, and rubidium, with the most preferred being potassium and sodium. In ophthalmic solutions, the potassium cation is preferred, but in inserts, the potassium and sodium forms are both preferred cations.

Other dibasic carbonic anhydrase inhibitors in the form of a mono-alkali metal salt can be used as well as those of formula I and II. Especially useful are those carbonic anhydrase inhibitors which have the sulfamoyl moiety (i.e., $-SO_2NH_2$) as a substituent. This can form the salt, $-SO_2N^-HM^+$, where $M^+$ is defined as above. Thus, carbonic anhydrase inhibitors such as p-sulfamoylbenzoic acid and 5-benzenesulfonamido-1,3,4-thiadiazol-2-sulfonamide can also be used when formulating the carbonic anhydrase inhibitor monoalkali metal salts into an ophthalmic preparation, e.g., from 0.1% to 5% by weight can be employed. The objective is to administer a dose of from 0.1 to 10 mg. per eye to the patient.

Thus, in a liquid vehicle from 0.1% to 15% is carbonic anhydrase inhibitor mono salt, the remainder being carrier.

The compounds of this invention are preferably administered in the form of ophthalmic pharmaceutical compositions adapted for topical administration to the eye such as solutions, ointments or as solid inserts. Formulations of these compounds may contain from 0.01 to 5% and especially 0.5% to 2% of medicament. Higher dosages as, for example, about 10%, for lower dosages can be employed provided the dose is effective in lowering intraocular pressure. As a unit dosage from between 0.001 to 10.0 mg., preferably 0.005 to 2.0 mg., and especially 0.1 to 1.0 mg. of the compound is generally applied to the human eye, generally on a daily basis.

These dosage values are believed accurate for human patients and are based on the pharmacology of carbonic anhydrase inhibitors and the action of other entities in the human eye. They reflect the best mode known. However, as with all medications dosage requirements are variable and must be individualized on the basis of the disease and the response of the patient. In rabbits the best mode is to employ a 5% to 10% weight formulation including suspensions, especially aqueous suspensions, medicated inserts, ointments and other pharmaceutically effective means of ocular drug delivery so long as it does not affect the stability of the delivered medicaments of carbonic anhydrase inhibitor salt for reducing intraocular pressure in rabbits with α-chymotrypsin induced ocular hypertension at a dose of 50 ml.

The pharmaceutical preparation which contains the compound may be conveniently admixed with a non-toxic pharmaceutical organic carrier, or with a pharmaceutically acceptable inorganic carrier. Typical of such pharmaceutically acceptable carriers are, for example, water, mixtures of water and watermiscible solvents such as lower alkanols or vegetable oils, petroleum based jelly, and including also from 0.5 to 5% by weight of hydroxyethyl cellulose, ethyl oleate, carboxymethyl cellulose, polyvinylpyrrolidone, and other water soluble ophthalmologically acceptable non-toxic polymers, for example, cellulose derivatives such as methyl cellulose, alkali metal carboxymethyl cellulose, hydroxyethyl cellulose, hydroxypropyl cellulose, hydroxypropylmethyl cellulose; acrylates such as polyacrylic acid salts, ethylacrylates; polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum and mixtures of these polymers. The pharmaceutical preparation may also contain non-toxic auxiliary substances such as emulsifying, preserving, wetting, bodying agents and the like, as for example, polyethylene glycols 200, 300, 400 and 600, carbowaxes 1,000, 1,500, 4,000, 6,000 and 10,000, antibacterial components such as quaternary ammonium compounds; phenylmercuric salts known to have cold sterilizing properties and which are non-injurious in use; thimerosal, methyl and propyl paraben, benzyl alcohol, phenyl ethanol; buffering ingredients such as alkal metal chloride, borate, acetate, gluconate buffers, and other conventional ingredients such as sorbitan monolaurate, triethanolamine, oleate, polyoxyethylene sorbitan monopalmitylate, dioctyl alkali metal sulfosuccinate, monothioglycerol, ethylenediamine tetracetic acid and the like. When buffers are used that comprise an alkali metal cation, it is most highly preferred that the alkali metal cation of the buffer is identical to the alkali metal cation of the carbonic anhydrase inhibitor.

Additonally, suitable ophthalmic vehicles can be used as carrier media for the present purpose including conventional phosphate buffer vehicle systems, isotonic boric acid vehicles, isotonic alkali chloride vehicles, tris and the like.

The pharmaceutical preparation may also be in the form of a solid insert. For example, one may use a solid water soluble polymer as the carrier for the medicament. Inserts are known in the art that are suitable for use with this include those set forth and described in British Pat. No. 15611, U.S. Pat Nos. 3,993,071; 3,986,510; 3,868,445; and 3,867,510 employing the formulation and fabrication techniques described therein. The polymer used to form the insert may be any water soluble, ophthalmologically acceptable, non-toxic polymer, for example, cellulose derivatives such as methyl cellulose, alkali metal carboxymethyl cellulose, hydroxyethyl cellulose, hydroxypropyl cellulose, hydroxypropylmethyl cellulose; acrylates such as polyacrylic acid salts, ethylacrylates; polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum and mixtures of said polymer.

If a solid insert is employed, it preferably is prepared from cellulose derivatives such as methyl cellulose, hydroxyethyl cellulose, hydroxypropyl Hydroxypropyl cellulose, one of the preferred polymers for the preparation of the insert is available in several polymeric forms, all of which are suitable in the preparation of these inserts. Thus, the product sold by Hercules, Inc. of Wilmington, Del., under the name KLUCEL such as KLUCEL HF, HWF, MF, GF, JF, LF and EF, which are intended for food or pharmaceutical use, are particularly useful. The molecular weight of these polymers useful for the purposes described herein may be at least 30,000 to about 1,000,000 or more.

Similarly, an ethylene oxide polymer having a molecular weight of up to 5,000,000 or greater, and preferably 100,000 to 5,000,000 can be employed.

Further, for example, POLYOX, a polymer supplied by Union Carbide Co., may be used having a molecular weight of about 50,000 to 5,000,000 or more and preferably 3,000,000 to 4,000,000. Other specific polymers which are useful are polyvinyl pyrrolidine having a molecular weight of from about 10,000 to about 1,000,000 or more, preferably up to about 350,000 and especially about 20,000 to 60,000; polyvinyl alcohol having a molecular weight of from about 30,000 to 1,000,000 or more, particularly about 400,000 and especially from about 100,000 to about 200,000; hydroxypropylmethyl cellulose having a molecular weight of from about 10,000 to 1,000,000 or more, particularly up to about 200,000 and especially about 80,000 to about 125,000; methyl cellulose having a molecular weight of from about 10,000 to about 1,000,000 or more, preferably up to about 200,000 and especially about 50 to 100,000; and CARBOPOL (carboxyvinyl polymer) of B. F. Goodrich and Co. designated as grades 934, 940 and 941.

For the purpose of this invention the type and molecular weight of the polymer is not critical. Any water soluble polymers can be used which have an average molecular weight which will afford dissolution of the polymer and, accordingly, the medicament in any desired length of time. The inserts, therefore, can be prepared to allow for retention and, accordingly, effectiveness in the eye for any desired period. The insert can be in the form of a square, rectangle, oval, circle, doughnut, semi-circle, ¼ moon shape, and the like. Preferably, the insert is in the form of a rod, doughnut, oval or ¼ moon. The insert can be readily prepared, for example, by dissolving the medicament and the polymer in a suitable solvent and evaporating the resulting solution to afford a thin film of the polymer which can then be subdivided to prepare inserts of appropriate size. Alternatively, the insert can be prepared by intimately admixing polymer and the medicament and thereafter molding the resulting mixture under the influence of heat and pressure to form a thin film. Preferably, the inserts are prepared by molding or extrusion procedures well known in the art. The molded or extruded product can then be subdivided to afford inserts of suitable size for administration in the eye.

The insert can be of any suitable size which readily fits into the eye. For example, castings or compression molded films having a thickness of about 0.25 mm. to 1.50 mm. can be subdivided to obtain suitable inserts. Rectangular segments of the cast or compressed film having a thickness between about 0.5 and 1.5 mm. can be cut to afford shapes such as rectangular plates of 4×5-20 mm. or ovals of comparable size. Similarly, extruded rods having a diameter between about 0.5 and 1.5 mm. can be cut into suitable sections to provide the desired amount of polymer. For example, rods of 1.0 to 1.5 mm. in diameter and about 2-20 mm. long are found to be satisfactory. The inserts may also be directly formed by injection molding. It is preferred that the ophthalmic inserts containing the medicament of the present invention be formed so that they are smooth and do not have any sharp edges or corners which could cause damage to the eye. Since the term smooth and sharp edges or corners are subjective terms, in this application these terms are used to indicate that excessive irritation of the eye will not result from the use of the insert.

The medicated ocular inserts can also contain plasticizers, buffering agents, appropriate inert fillers, and preservatives. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di- and tripropylene glycol, hydroxypropyl sucrose and the like. Typically, such plasticizers can be present in the medicated ophthalmic insert in an amount ranging from up to 1 to about 30% by weight. A particularly preferred plasticizer is water which is present in amounts of at least about 5% up to about 40%. In actual practice, a water content of from about 10% to about 20% is preferred since it may be easily accomplished and adds the desired softness and pliability to the insert.

When plasticizing the solid medicinal product with water, the product is contacted with air having a relative humidity of at least 40% until said product picks up at least about 5% water and becomes softer and more pliable. In a preferred embodiment, the relative humidity of the air is from about 60% to about 99% and the contact is continued until the water is present in the product in amounts of from about 10% to about 20%.

Suitable water soluble preservatives which may be employed in the insert are alkali bisulfate, alkali thiosulfate, ascorbate, benzalkonium chloride, chlorobutanol, thimerosal, phenylmercuric acetate, phenylmercuric borate, parabens, benzyl alcohol and phenyl ethanol. These agents may be present in amounts of from 0.001 to 5% by weight of solid insert, and preferably 0.1 to 2%.

It is highly preferred that the solid inserts of this invention are available for use by the patient in a pathogen free condition. Thus, it is preferred to sterilize the inserts and so as insure against recontamination, the sterilization is preferably conducted after packaging. The best mode of sterilizing is to employ ionizing irradiation including irradiation emanating from Cobalt 60 or high energy electron beams.

After packaging a convenient quantity of inserts, usually a single dose, the package is exposed to a sterilizing quantity of radiation. The preferred packaging employs sealing the inserts between layers of film or foil and then sealing or laminating the layers together about the edges. The techniques for performing the sterilization are well known and accepted, for example, as outlined in International Atomic Energy Commission, *Code of Practice for Radiosterilization of Medical Products*, 1967, pp. 423-431; and Block, *Disinfection, Sterilization and Preservation*, 2nd E., Lea & Febiger, Philadelphia, 1977, pp. 542-561.

The required quantity of irradiation can be determined experimentally by testing irradiated inserts for viable bacteria. Generally, the amount of irradiation desired to achieve sterilization is defined by the $D_{10}$ value. The $D_{10}$ value is the radiation dose that will reduce a given population of organisms by a factor of 10. Based on $D_{10}$ values, experimentally obtained for *Bacillus pumilus*, and presterilization contamination levels, a dose of 1.36 megarads is effective in obtaining a sterile product.

The following Examples illustrate the preparation of the mono-alkali metal salts of the carbonic anhydrase inhibitors of this invention.

EXAMPLE 1

Preparation of 4,5-dichloro-m-benzenedisulfonamide Mono Sodium Salt

To a solution of sodium methoxide (5.0 millimoles) in methanol (100 ml), freshly generated by the careful portionwise additions of sodium (1.15 g, 5.0 millimole) to methanol (100 ml.), is added 4,5-dichloro-m-benzenedisulfonamide (15.16 g, 5.0 millimole) with stirring at 25° C. The resulting mixture is stirred at 25° C. for 30 minutes to provide a colorless solution which is filtered. Evaporation of the clear, colorless filtrate at 40° C. in vacuo provides a solid residue which is dried in vacuo at 80° C. for 16 hours to provide analytically pure 4,5-dichloro-m-benzenedisulfonamide mono sodium salt as a colorless solid (14.0 g., 85%), m.p./252°-244° C.

Anal. Calcd. for $C_2H_5Cl_2N_2O_4S_2Na$: C, 22.03; H, 1.54; N, 8.56. Found: C, 22.31; H, 1.55; N, 8.54.

EXAMPLE 2

Preparation of 4,5-dichloro-m-benzenedisulfonamide Mono Potassium Salt

Using essentially the procedure as described in Example 1, but replacing the sodium methoxide with an equivalent amount of potassium hydroxide, there is obtained 4,5-dichloro-m-benzenedisulfonamide mono potassium salt as a solid.

EXAMPLE 3

Preparation of 4,5-dichloro-m-benzenedisulfonamide Mono Rubidium Salt

Using essentially the procedure described in Example 1, but replacing the sodium methoxide with an equivalent amount of rubidium hydroxide, there is obtained 4,5-dichloro-m-benzenedisulfonamide mono rubidium salt.

In an analagous manner using equivalent quantities of materials, but substituting in place of the 4,5-dichloro-m-benzenedisulfonamide of Examples 1, 2, and 3, the following:

N-[5-(aminosulfonyl)-3-methyl-1,3,4-thiadiazol-2(3H)-ylidene]acetamide;
N-[5-(aminosulfonyl)-1,3,4-thiadiazol-2-(3H)-ylidene]-acetamide;
p-sulfamoylbenzoic acid
N-[5-(aminosulfonyl)-1,3,4-thiadiazol-2-yl]-propanamide;
N-[5-(aminosulfonyl)-1,3,4-thiadiazol-2-yl]-butanamide; and
5-benzenesulfonamido-1,3,4-thiadiazol-2-sulfonamide, there are respectively prepared the monosodium, mono potassium and mono rubidium salts thereof.

In the reduction of introacular pressure, and especially the treatment of mammalian glaucoma, additional agents particularly agents that work by a mode of action other than carbonic anhydrase inhibition can be employed in combination with the monosodium salts of this invention. In the practice of such combination therapy each agent will generally be employed in from 50 to 100% of the dosage that would have been employed had the respective agent been used in single entity therapy. It is feasible, however, to employ from 50 to 150% of the usual dosage of each entity when such is used in the combination. Examples of such additional therapeutic entities that may be employed in combination with carbonic anhydrase inhibitors are pilocarpine, particularly pilocarpine hydrochloride and other pilocarpine salts typically used in ophthalmology; epinephrine; and the β-blocking agents known to reduce intraocular pressure, particularly timolol.

What is claimed is:

1. An ophthalmic composition for lowering intraocular pressure comprising from 0.01 to 2% by weight of a mono alkali metal salt of a dibasic carbonic anhydrase inhibitor and an ophthalmologically acceptable carrier for topical application, where the carbonic anhydrase inhibitor is selected from the group consisting of N-[5-(amino-sulfonyl)-3-methyl-1,3,4-thiadiazol-2(3H)-ylidene]-acetamide; N-[5-(amino-sulfonyl)-1,3,4-thiadiazol-2-yl]propanamide; N-[5-(aminosulfonyl)-1,3,4-thiadiazol-2-yl]butanamide and 5-benzenesulfonamido-1,3,4-thiadiazol-2-sulfonamide.

2. A composition according to claim 11 where the carrier is an isotonic aqueous solution.

3. A composition according to claim 1 where there is included a preservative.

4. The composition of claim 1 where the carrier comprises a solid water soluble polymer.

5. An ophthalmologically acceptable water solid polymeric insert comprising from 0.01 to 2% by weight of a mono potassium or mono sodium salt of a carbonic anhydrase inhibitor selected from the group consisting of N-[5-(amino-sulfonyl)-3-methyl-1,3,4-thiadiazol-2(3H)-ylidene]acetamide; N-[5-(amino-sulfonyl)-1,3,4-thiadiazol-2-yl]propanamide; N-[5-(aminosulfonyl)-1,3,4-thiadiazol-2-yl]butanamide and 5-benzenesulfonamido-1,3,4,-thiadiazol-2-sulfonamide.

6. An insert according to claim 5 where the polymeric carrier is a polymer soluble in lacrimal fluids.

7. An insert according to claim 3 where the salt is the potassium salt.

8. An insert according to claim 3 where the salt is the sodium salt.

9. A method of lowering intraocular pressure which comprises topically applying to the eye an effective intraocular pressure lowering amount of a mono alkali metal salt of a dibasic carbonic anhydrase inhibitor selected from the group consisting of N-[5(amino-sulfonyl)-3-methyl-1,3,4-thiadiazol-2(3H)-ylidene]-acetamide, N-[5-(aminosulfonyl)-1,3,4-thiadiazol-2-yl]-propanamide, N-[5-(aminosulfonyl)-1,3,4-thiadiazol-2-yl]-butanamide and 5-benzenesulfonamide-1,3,4-thiadiazol-2-sulfonamide.

10. A method according to claim 9 where the carbonic anhydrase inhibitor is the sodium, potassium, or rubidium salt of N-[5-(aminosulfonyl)-3-methyl-1,3,4-thiadiazol-2(3H)-ylidene]acetamide; N-[5-(aminosulfonyl)-3-methyl-1,3,4-thiadiazol-2(3H)-ylidene]-acetamide; N-[5-(aminosulfonyl)-1,3,4-thiadiazol-2-yl]propanamide; N-[5-(aminosulfonyl)-1,3,4-thiadiazol-2-yl]butanamide and 5-benzenesulfonamido-1,3,4-thiadiazol-2-sulfonamide.

11. A method according to claim 10 where the salt is the potassium salt.

12. A method according to claim 9 where the salt is the sodium salt.

* * * * *